United States Patent [19]

Kobayashi et al.

[11] 4,322,420
[45] Mar. 30, 1982

[54] METHOD OF USING 4-ANILINOQUINAZOLINE DERIVATIVES AS ANALGESIC AND ANTI-INFLAMMATORY AGENTS

[75] Inventors: Shinsaku Kobayashi; Katsuo Kamoshita, both of Tokyo; Shigeki Nagai, Ube; Takeo Honda, Ube; Kiroku Oda, Ube; Katsutoshi Fujii, Ube; Takashi Kobayashi, Ube; Mikio Kojima, Ube, all of Japan

[73] Assignees: Sankyo Company Limited, Tokyo; UBE Industries, Ube, both of Japan

[21] Appl. No.: 74,343

[22] Filed: Sep. 11, 1979

[30] Foreign Application Priority Data

Sep. 11, 1978 [JP] Japan .................... 53/111484

[51] Int. Cl.³ .................. A61K 31/505; C07D 239/94
[52] U.S. Cl. ..................................... 424/251; 544/293
[58] Field of Search ....................... 544/293; 424/251

[56] References Cited

U.S. PATENT DOCUMENTS

| | | | |
|---|---|---|---|
| 1,724,086 | 8/1929 | Hentrich et al. | 544/293 |
| 3,541,094 | 11/1970 | Lutz et al. | 544/293 |
| 3,560,619 | 2/1971 | Harrison et al. | 424/251 |
| 3,985,749 | 10/1976 | Foster | 544/293 |
| 4,041,030 | 8/1977 | Fauran et al. | 424/251 |

OTHER PUBLICATIONS

Christensen et al., JACS, 68, 1946, pp. 1306–1308.

Primary Examiner—Donald G. Daus
Assistant Examiner—D. B. Springer
Attorney, Agent, or Firm—Frishauf, Holtz, Goodman & Woodward

[57] ABSTRACT

A method of using 4-anilinoquinazoline derivatives of formula (I):

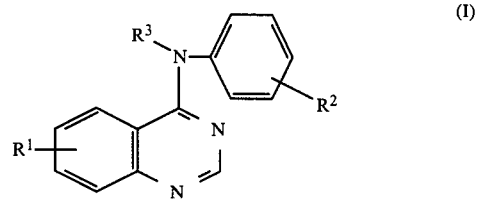

(in which:

$R^1$ represents a hydrogen atom, a halogen, atom, a trifluoromethyl group or a nitro group;

$R^2$ represents a hydrogen atom, a $C_1$–$C_4$ alkyl group, an alkoxy group or a halogen atom; and $R^3$ represents a hydrogen atom or a $C_1$–$C_4$ alkyl group)

and pharmaceutically acceptable salts thereof are, provided that $R^1$ does not represents a hydrogen atom or a chlorine atom in the 6- position when $R^2$ and $R^3$ both represent hydrogen atoms, as an analgesic and anti-inflammatory in the treatment of mammals. These compounds can be prepared by heating the appropriate 4-haloquinazoline with an appropriate aniline or aniline derivative.

11 Claims, No Drawings

METHOD OF USING 4-ANILINOQUINAZOLINE DERIVATIVES AS ANALGESIC AND ANTI-INFLAMMATORY AGENTS

BACKGROUND OF THE INVENTION

The present invention relates to a series of new 4-anilinoquinazoline derivatives, to a process for their preparation and to their use as analgesic and anti-inflammatory agents.

A wide range of analgesic and anti-inflammatory agents is available, suitable for treating pain of all intensity from mild (treated with aspirin, paracetamol or the like) to intense (treated with a narcotic analgesic, such as morphine or pentazocine). However, all of these known compounds have side effects, which may range from stomach irritation in the case of aspirin to dizziness, drowsiness and nausea and, in the case of the narcotic analgesics, may include dependence. The incidence and severity of these side effects varies from person to person and there is, therefore, a continuing need for new classes of analgesic for administration to persons to whom administration of existing analgesics would be inappropriate.

We have now surprisingly discovered that a class of 4-anilinoquinazoline derivatives possesses analgesic and anti-inflammatory activity comparable with, but in many cases substantially better than, that of aspirin. Although aminoquinazolines, including 4-anilinoquinazoline and 4-anilino-6-chloroquinazoline, are known [see, for example, J. Org. Chem., 41, 2646 (1976) and U.S. Pat. No. 3,985,749], they have hitherto been proposed for use in the treatment of coccidiosis and we are not aware of any prior suggestions that they have analgesic or anti-inflammatory activity.

BRIEF SUMMARY OF INVENTION

It is, therefore, an object of the present invention to provide a series of new 4-anilinoquinazoline derivatives useful as analgesic and anti-inflammatory agents.

It is a further object of the invention to provide a new process for preparing such 4-anilinoquinazoline derivatives.

It is a still further object of the invention to provide pharmaceutical compositions containing the new 4-anilinoquinazoline derivatives.

The 4-anilinoquinazoline derivatives which may be prepared by the process of the invention are those compounds of formula (I):

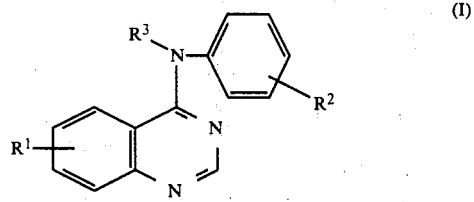

in which:
$R^1$ represents a hydrogen atom, a halogen atom, a trifluoromethyl group or a nitro group;
$R^2$ represents a hydrogen atom, an alkyl group, an alkoxy group or a halogen atom; and
$R^3$ represents a hydrogen atom or an alkyl group; and pharmacologically acceptable acid addition salts thereof.

Of these compounds, all are per se new, except those compounds in which $R^1$ represents a hydrogen atom or a chlorine atom in the 6-position and $R^2$ and $R^3$ both represent hydrogen atoms. Throughout this Specification, the numbering adopted for the ring systems in the anilinoquinazoline derivatives of the invention is as shown below:

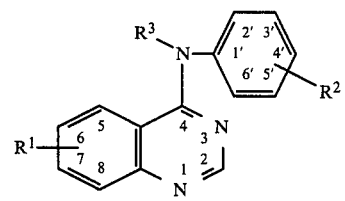

The process of the invention comprises heating a haloquinazoline derivative of formula (II):

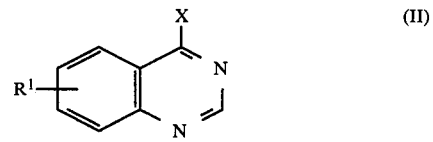

(in which $R^1$ is a hydrogen atom, a halogen atom, a trifluoromethyl group or a nitro group and X represents a halogen atom) with aniline or an aniline derivative of formula (III):

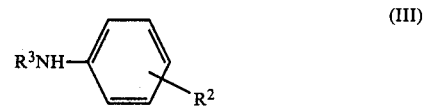

(in which $R^2$ represents a hydrogen atom, an alkyl group, an alkoxy group or a halogen atom and $R^3$ represents a hydrogen atom or an alkyl group).

The invention also provides a pharmaceutical composition comprising a pharmaceutically acceptable carrier or diluent and, as active ingredient, one or more of the new 4-anilinoquinazoline derivatives of the present invention.

DETAILED DESCRIPTION OF INVENTION

In the above formulae, $R^1$ represents a hydrogen atom, a halogen atom, a trifluoromethyl group or a nitro group and, where $R^1$ represents a halogen atom, it is preferably a fluorine, chlorine or bromine atom.

Where $R^2$ represents an alkyl group, this is preferably a lower alkyl group and most preferably a straight or branched chain alkyl group having from 1 to 4 carbon atoms, e.g. a methyl, ethyl, n-propyl, isopropyl, n-butyl or isobutyl group. Where $R^2$ represents an alkoxy group, this is preferably a lower alkoxy group and most preferably a straight or branched chain alkoxy group having from 1 to 4 carbon atoms, e.g. a methoxy, ethoxy, n-propoxy, isopropoxy, n-butoxy or isobutoxy group. Where $R^2$ represents a halogen atom, this is preferably a fluorine, chlorine or bromine atom.

Where $R^3$ represents an alkyl group, this is preferably a lower alkyl group and more preferably a straight or branched chain alkyl group having from 1 to 4 carbon atoms e.g. a methyl, ethyl, n-propyl, isopropyl, n-butyl or isobutyl group.

Among the compounds of the invention where R³ represents a hydrogen atom, a preferred class are those compounds of formula (Ia):

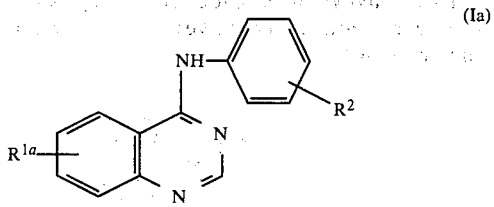

(in which R¹ᵃ represents a halogen atom or a trifluoromethyl group and R² is as defined above, provided that R¹ᵃ does not represent a chlorine atom at the 6-position when R² represents a hydrogen atom) and pharmacologically acceptable acid addition salts thereof.

More preferred compounds within this class are those in which R¹ᵃ represents a halogen atom at the 7-position or a trifluoromethyl group at the 7- or 8-position and R² is as defined above and most preferred compounds are those in which R¹ᵃ represents a chlorine atom at the 7-position or a trifluoromethyl group at the 7- or 8-position and R² represents a hydrogen atom, a methyl group, a methoxy group or a chlorine atom.

Among the compounds in which R³ represents an alkyl group, particularly preferred compounds are those in which:

R¹ represents a hydrogen atom, or a chlorine atom, a trifluoromethyl group or a nitro group at the 7- or 8-position;

R² represents a hydrogen atom, or a methyl group, ethyl group, methoxy group, ethoxy group or chlorine atom at the 4'-position; and R³ represents a methyl group or an ethyl group.

Examples of compounds in accordance with the present invention are listed below. The numbers appended to the compounds in the following list are used to identify them subsequently in the Specification.

1. 4-Anilino-5-chloroquinazoline.
2. 4-Anilino-5-chloroquinazoline hydrochloride.
3. 6-Chloro-4-(3'-methylanilino)quinazoline.
4. 6-Chloro-4-(3'-methylanilino)quinazoline hydrochloride.
5. 4-Anilino-7-chloroquinazoline.
6. 4-Anilino-7-chloroquinazoline hydrochloride.
7. 7-Chloro-4-(4'-methylanilino)quinazoline.
8. 7-Chloro-4-(4'-methylanilino)quinazoline hydrochloride.
9. 7-Chloro-4-(4'-methoxyanilino)quinazoline.
10. 7-Chloro-4-(4'-methoxyanilino)quinazoline hydrochloride.
11. 7-Chloro-4-(2'-chloroanilino)quinazoline.
12. 7-Chloro-4-(2'-chloroanilino)quinazoline hydrochloride.
13. 4-Anilino-8-chloroquinazoline.
14. 4-Anilino-8-chloroquinazoline hydrochloride.
15. 4-Anilino-7-fluoroquinazoline.
16. 4-Anilino-7-fluoroquinazoline hydrochloride.
17. 4-Anilino-7-trifluoromethylquinazoline.
18. 4-Anilino-7-trifluoromethylquinazoline hydrochloride.
19. 4-Anilino-8-trifluoromethylquinazoline.
20. 4-Anilino-8-trifluoromethylquinazoline hydrochloride.
21. 6-Chloro-4-(4'-chloroanilino)quinazoline.
22. 6-Chloro-4-(4'-chloroanilino)quinazoline hydrochloride.
23. 6-Chloro-4-(4'-methylanilino)quinazoline.
24. 6-Chloro-4-(4'-methylanilino)quinazoline hydrochloride.
25. 5-Chloro-4-(3'-chloroanilino)quinazoline.
26. 5-Chloro-4-(3'-chloroanilino)quinazoline hydrochloride.
27. 6-Chloro-4-(2'-chloroanilino)quinazoline.
28. 6-Chloro-4-(2'-chloroanilino)quinazoline hydrochloride.
29. 4-(4'-Bromoanilino)-6-chloroquinazoline.
30. 4-(4'-Bromoanilino)-6-chloroquinazoline hydrochloride.
31. 6-Chloro-4-(2'-methoxyanilino)quinazoline.
32. 6-Chloro-4-(2'-methoxyanilino)quinazoline hydrochloride.
33. 7-Chloro-4-(4'-chloroanilino)quinazoline.
34. 7-Chloro-4-(4'-chloroanilino)quinazoline hydrochloride.
35. 7-Chloro-4-(2'-methylanilino)quinazoline.
36. 7-Chloro-4-(2'-methylanilino)quinazoline hydrochloride.
37. 6-Chloro-4-(2'-methylanilino)quinazoline.
38. 6-Chloro-4-(2'-methylanilino)quinazoline hydrochloride.
39. 7-Chloro-4-(3'-chloroanilino)quinazoline.
40. 7-Chloro-4-(3'-chloroanilino)quinazoline hydrochloride.
41. 7-Chloro-4-(3'-methylanilino)quinazoline.
42. 7-Chloro-4-(3'-methylanilino)quinazoline hydrochloride.
43. 7-Chloro-4-(4'-ethylanilino)quinazoline.
44. 7-Chloro-4-(4'-ethylanilino)quinazoline hydrochloride.
45. 4-(4'-n-Butylanilino)-7-chloroquinazoline.
46. 4-(4'-n-Butylanilino)-7-chloroquinazoline hydrochloride.
47. 7-Chloro-4-(4'-ethoxyanilino)quinazoline.
48. 7-Chloro-4-(4'-ethoxyanilino)quinazoline hydrochloride.
49. 8-Chloro-4-(3'-chloroanilino)quinazoline.
50. 8-Chloro-4-(3'-chloroanilino)quinazoline hydrochloride.
51. 4-(4'-Methoxyanilino)-7-trifluoromethylquinazoline.
52. 4-(4'-Methoxyanilino)-7-trifluoromethylquinazoline hydrochloride.
53. 4-(N-Methylanilino)quinazoline.
54. 4-(N-Methylanilino)quinazoline hydrochloride.
55. 7-Chloro-4-(N-methylanilino)quinazoline.
56. 7-Chloro-4-(N-methylanilino)quinazoline hydrochloride.
57. 7-Chloro-4-(N-ethylanilino)quinazoline.
58. 7-Chloro-4-(N-ethylanilino)quinazoline hydrochloride.
59. 7-Chloro-4-(N-methyl-4'-methylanilino)quinazoline.
60. 7-Chloro-4-(N-methyl-4'-methylanilino)quinazoline hydrochloride.
61. 7-Chloro-4-(4'-ethyl-N-methylanilino)quinazoline.
62. 7-Chloro-4-(4'-ethyl-N-methylanilino)quinazoline hydrochloride.
63. 7-Chloro-4-(4'-methoxy-N-methylanilino)quinazoline.
64. 7-Chloro-4-(4'-methoxy-N-methylanilino)quinazoline hydrochloride.
65. 7-Chloro-4-(4'-ethoxy-N-methylanilino)quinazoline.
66. 7-Chloro-4-(4'-ethoxy-N-methylanilino)quinazoline hydrochloride.

67. 7-Chloro-4-(4'-chloro-N-methylanilino)quinazoline.
68. 7-Chloro-4-(4'-chloro-N-methylanilino)quinazoline hydrochloride.
69. 7-Chloro-4-(4'-chloro-N-ethylanilino)quinazoline.
70. 7-Chloro-4-(4'-chloro-N-ethylanilino)quinazoline hydrochloride.
71. 8-Chloro-4-(N-methylanilino)quinazoline.
72. 8-Chloro-4-(N-methylanilino)quinazoline hydrochloride.
73. 4-(N-Methylanilino)-7-trifluoromethylquinazoline.
74. 4-(N-Methylanilino)-7-trifluoromethylquinazoline hydrochloride.
75. 4-(4'-Methoxy-N-methylanilino)-7-trifluoromethylquinazoline.
76. 4-(4'-Methoxy-N-methylanilino)-7-trifluoromethylquinazoline hydrochloride.
77. 4-(N-Methylanilino)-8-trifluoromethylquinazoline.
78. 4-(N-Methylanilino)-8-trifluoromethylquinazoline hydrochloride.
79. 4-(N-Methylanilino)-7-nitroquinazoline.
80. 4-(N-Methylanilino)-7-nitroquinazoline hydrochloride.

Of these compounds, particularly valuable compounds have been found to be Compounds Nos. 5, 17, 55 and 73, as well as their acid addition salts, particularly the hydrochlorides (that is to say, Compounds Nos. 6, 18, 56 and 74); of these, the most preferred compound is Compound No. 5 and its acid addition salts, particularly the hydrochloride, Compound No. 6.

The compounds of formula (I) can be prepared by heating a corresponding haloquinazoline derivative of formula (II):

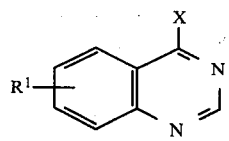

with aniline or an aniline derivative of formula (III):

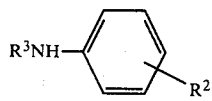

(in which $R^1$, $R^2$, $R^3$ and X are as defined above). X is preferably a chlorine, bromine or iodine atom.

The process of the invention is preferably carried out in the presence of a solvent, although the nature of the solvent is not critical, provided that it has no adverse effect upon the reaction. Preferred solvents are: alcohols, such as methanol or ethanol; ethers, such as tetrahydrofuran or dioxan; aromatic hydrocarbons, such as benzene or toluene; or halogenated aromatic hydrocarbons, such as 2,4-dichlorobenzene. The precise ratio of haloquinazoline derivative (II) to aniline or aniline derivative (III) is also not critical; however, for reasons of economy, we prefer to employ approximately equimolar amounts of the two reagents. Since the reaction is exothermic, the reaction temperature, too, is not critical. The reaction is most conveniently carried out by heating the reaction mixture to approximately the boiling temperature of the solvent employed. The reaction can be accelerated by the use of a catalytic amount of a mineral acid, such as hydrochloric acid or sulphuric acid.

The reagents can be mixed in any order; for example, the haloquinazoline derivative (II) can be mixed with the appropriate amount of the aniline or aniline derivative (III), after which the solvent is added and the mixture is heated; alternatively, the aniline or aniline derivative (III) is added to a solution containing the appropriate amount of the haloquinazoline derivative (II) and the resulting solution is heated. The time required for the reaction will depend upon the nature of the reagents, the reaction temperature and other conditions; however, the reaction will normally take from 5 minutes to 5 hours.

When the reaction is carried out under the conditions described above, the compound of formula (I) is normally obtained in the form of its salt with the hydrohalic acid HX, although the compound (I) is occasionally obtained in the form of the free base, in which case a portion of the aniline derivative (III) has acted as an acid binding agent, and this can be favoured if the amount of aniline derivative (III) employed is greater than equimolar. However, a better way of ensuring that the compound (I) is obtained in the form of a free base is to carry out the reaction in the presence of a base (e.g. triethylamine) as acid binding agent. In this case, the preferred procedure is to dissolve the haloquinazoline derivative (II) in a water-immiscible organic solvent (such as benzene, toluene or 2,4-dichlorobenzene), to add to the resulting solution the desired amount (preferably an equimolar amount) of the aniline or aniline derivative (III) and 1.2 times an equimolar amount of an acid binding agent, and then to heat the reaction mixture to about the boiling temperature of the solvent employed for a period of from 3 to 5 hours.

When the reaction is complete, the desired compound may be recovered from the reaction mixture by conventional means. For example, one suitable recovery sequence comprises: if necessary, distilling off the solvent from the reaction mixture; optionally adding the residue to water or to an inert organic solvent and then separating the compound by filtration; and finally recrystallizing the compound from a suitable organic solvent.

Where the desired compound is obtained in the form of a free base by carrying out the reaction in the presence of an acid binding agent and a water-immiscible organic solvent, a preferred recovery sequence comprises: adding water to the reaction mixture; separating and then drying the organic phase; distilling the solvent from this organic phase under reduced pressure; and finally recrystallizing the desired compound from a suitable organic solvent.

Where the compound has been produced in the form of an hydrohalide salt and it is desired to obtain the free base, the salt is treated with a dilute aqueous solution of an alkali (such as sodium hydroxide or potassium hydroxide) and the precipitated product is collected by filtration, washed with water and recrystallized from a suitable organic solvent; this may be carried out either before or after separation of the hydrohalide salt from the initial reaction mixture.

Where the free base form of the compound of formula (I) has been obtained, this may, if desired, be converted to a pharmacologically acceptable acid addition salt by conventional salification techniques. Suitable salts include acid addition salts of mineral acids (such as hydrochloric acid, hydrobromic acid or hydroiodic acid) or acid addition salts of organic acids (such as oxalic acid, maleic acid, fumaric acid, tartaric acid or citric acid).

Surprisingly, the anilinoquinazoline derivatives of the present invention have excellent analgesic and anti-inflammatory activities, as demonstrated by the following tests.

TEST FOR ANALGESIC ACTIVITY

This test employs a bradykinin-induced nociceptive stimulus and is a partially modified version of the test described by Deffenu [J. Pharm. Pharmac. 18, 135 (1966)] and Blane [J. Pharm. Pharmac., 19, 367 (1967)]. The test animals were female Hartley guinea pigs having a body weight of from 350 g to 400 g. The guinea pigs were divided into groups, each group containing from 5 to 10 animals. The test animals were cannulated into the carotid artery retrogradely under the anesthesia induced by intraperitoneal injection of 20 mg/kg of pentobarbital. The guinea pigs were allowed to recover from the anesthesia for at least 3 hours before the tests commenced.

The test compounds listed in the following Table 1 were administered orally. Immediately before administration of each test compound and then 15, 30, 60, 90 and 120 minutes after administration, each guinea pig was administered with 0.5 μg of bradykinin through the cannula. Turning of the head or twisting of the front legs upon injection was taken as a sign of nociceptive response. The test compounds were administered at various doses and the inhibition rate was determined accordingly.

TEST FOR ANTI-INFLAMMATORY ACTIVITY

Male Wistar-Imamichi rats, each weighing approximately 150 g, were used in these experiments and were divided into groups, each containing 5 animals. Each of the test compounds listed in Table 1 was administered orally, at various doses, to the rats and then, 30 minutes after oral administration, 0.05 ml of a 1% w/v carrageenin suspension was subcutaneously injected into the sole of the right hind paw to induce oedema. The volume of the paw was measured both before and 3 hours after injection of the carrageenin by the method of Winder et al [Arch. Int. Pharmacodyn. 112, 174 (1957)]. The difference between the volume of the paw before and after injection was defined as the oedema intensity. The inhibition rate was the ratio of the oedema intensity in groups to which the test compounds had been administered to control groups, to which no test compounds had been administered.

For both of the above tests, the $ID_{50}$ was calculated by the method of Litchfield and Wilcoxon [J. Pharmacol. Exptl. Therap. 96, 99 (1949)] on the basis of the inhibition rates obtained as described above. The results are shown in Table 1, in which the compounds of the invention are identified by the numbers heretofore assigned to them.

TABLE 1

| Test Compound | $ID_{50}$ (mg/kg) per os | |
|---|---|---|
| | Analgesic Activity | Anti-inflammatory Activity |
| 5 | 25 | 28 |
| 17 | 16.5 | 20 |
| 55 | 50 | 36 |
| 73 | 31 | 15.5 |
| Controls | | |
| Mefenamic acid | 72 | 50 |

TABLE 1-continued

| Test Compound | $ID_{50}$ (mg/kg) per os | |
|---|---|---|
| | Analgesic Activity | Anti-inflammatory Activity |
| Aspirin | 280 | 145 |

It is apparent from the results shown above that the compounds of the invention have valuable analgesic and anti-inflammatory activities comparable with or better than those of aspirin and mefenamic acid.

The compounds of the invention can be administered orally in the form of tablets, capsules, granules, powders or syrups or through the intestines in the form of a suppository. The dosage depends on the symptoms, age and body weight of the patient, but is usually from 50 mg to 2000 mg per day for an adult, in a single dose or in divided doses.

The preparation of the compounds of the invention is further illustrated by the following non-limiting Examples.

EXAMPLE 1

4-Anilino-5-chloroquinazoline hydrochloride (Compound No. 2)

A solution of 3.0 g of 4,5-dichloroquinazoline and 1.4 g of aniline in 20 ml of ethanol was heated, whereupon a violet reaction occurred and the reaction mixture solidified. After cooling, the solidified product was collected and recrystallized from ethanol to give 1.8 g (yield 46%) of the desired Compound No. 2 in the form of a pale yellow powder melting at 263°–267° C. (with decomposition).

Elemental Analysis: Calculated for $C_{14}H_{11}N_3Cl_2$: C, 57.55%; H, 3.80%; N, 14.38%. Found: C, 57.70%; H, 4.15%; N, 14.25%.

EXAMPLE 2

6-Chloro-4-(3'-methylanilino)quinazoline hydrochloride (Compound No. 4)

4.0 g of 4,6-dichloroquinazoline were dissolved in 50 ml of dioxan and then 2.0 g of m-toluidine were added. The mixture was then heated to reflux for 3 hours at 100° C. After completion of the reaction, the precipitated product was collected by filtration and recrystallized from ethanol to afford 3.7 g (yield 60%) of the desired Compound No. 4, in the form of pale yellow needles melting at 251°–254° C. (with decomposition).

Elemental Analysis: Calculated for $C_{15}H_{13}N_3Cl_2$: C, 59.01%; H, 4.26%; N, 13.77%. Found: C, 58.70%; H, 4.20%; N, 13.40%.

EXAMPLES 3–5

Following the procedures described in Examples 1 and 2, the hydrochlorides listed and identified in Table 2 were obtained.

TABLE 2

| Ex. No. | Cpd. No. | Melting point | Appearance | Yield |
|---|---|---|---|---|
| 3 | 6 | 271–273° C. (decomposition) | pale yellow needles | 38% |
| 4 | 22 | 276–280° C. (decomposition) | pale yellow needles | 46% |
| 5 | 24 | 264–265° C. (decomposition) | yellow powder | 62% |

EXAMPLE 6

4-Anilino-7-chloroquinazoline (Compound No. 5)

8.0 g of 4,7-dichloroquinazoline were dissolved in 250 ml of benzene, and then 4.0 g of aniline and 4.8 g of triethylamine were added to the solution. The resulting mixture was heated to reflux for 5 hours, with stirring. After completion of the reaction, 200 ml of water were added to the reaction mixture. The mixture was shaken and the benzene phase was separated and dried over anhydrous sodium sulphate. The benzene was distilled off and the resulting crystals were recrystallized from ethyl acetate to give 8.5 g (yield 83%) of the desired Compound No. 5 in the form of colourless granules having a melting point of 215°–217° C.

Elemental Analysis: Calculated for $C_{14}H_{10}N_3Cl$: C, 65.76%; H, 3.94%; N, 16.43%. Found: C, 65.81%; H, 3.61%; N, 16.29%.

EXAMPLES 7–12

Following the procedure described in Example 6, there were obtained the compounds listed in Table 3, in which the compounds obtained are identified by the numbers heretofore assigned to them.

TABLE 3

| Ex. No. | Cpd. No. | Melting Point | Appearance | Yield |
|---|---|---|---|---|
| 7 | 25 | 133–135° C. | colourless powder | 41% |
| 8 | 27 | 245–251° C. | yellow granules | 38% |
| 9 | 29 | 218–220° C. | pale yellow needles | 24% |
| 10 | 31 | 137–139° C. | colourless needles | 59% |
| 11 | 33 | 206–208° C. | colourless powder | 35% |
| 12 | 35 | 155–158° C. | colourless needles | 52% |

EXAMPLE 13

4-Anilino-8-chloroquinazoline (Compound 13)

15 ml of ethanol were added to a mixture of 3.0 g of 4,8-dichloroquinazoline and 1.9 g of aniline, and then the mixture was heated. The reagents dissolved and immediately solidified. After cooling, the solidified product was collected, washed with ethanol and then recrystallized from ethanol to give 1.9 g (yield 48%) of the desired Compound No. 13 in the form of colourless crystals having a melting point of 206° C. (with decomposition).

Elemental Analysis: Calculated for $C_{14}H_{10}N_3Cl.0.5H_2O$: C, 63.52%; H, 4.19%; N, 15.87%. Found: C, 63.50%; H, 4.30%; N, 15.45%.

EXAMPLES 14–22

Following the procedure described in Example 13, the hydrochlorides listed in Table 4 were obtained; these compounds are identified by the numbers heretofore assigned to them.

TABLE 4

| Ex. No. | Cpd. No. | Melting point | Appearance | Yield |
|---|---|---|---|---|
| 14 | 8 | >280° C. | yellow powder | 33% |
| 15 | 12 | 237–241° C. (decomposition) | pale yellow powder | 43% |
| 16 | 38 | 200–203° C. | pale yellow powder | 52% |
| 17 | 40 | 286–290° C. (decomposition) | pale yellow powder | 33% |
| 18 | 42 | 248–251° C. (decomposition) | yellow powder | 38% |
| 19 | 44 | >280° C. | yellow granules | 40% |
| 20 | 46 | 247–250° C. (decomposition) | yellow powder | 53% |
| 21 | 48 | 265–268° C. (decomposition) | pale yellow needles | 55% |
| 22 | 50 | 224° C. (decomposition) | pale yellow powder | 55% |

EXAMPLE 23

4-Anilino-7-trifluoromethylquinazoline (Compound No. 17)

2.5 g of 4-chloro-7-trifluoromethylquinazoline were dissolved in 10 ml of ethanol, and 1.0 g of aniline was added to the solution. Reaction occurred violently and the reaction mixture solidified immediately. After cooling, the solidified product was collected and washed with ethanol. The resulting crystals were pulverized and added to a dilute aqueous solution of sodium hydroxide. Insolubles were filtered off and recrystallized from ethanol to give 1.7 g (yield 60%) of the desired Compound No. 17 in the form of colourless plates melting at 230°–232° C.

Elemental Analysis: Calculated for $C_{15}H_{10}N_3F_3$: C, 62.28%; H, 3.48%; N, 14.53%. Found: C, 62.50%; H, 3.50%; N, 14.50%.

EXAMPLE 24

7-Chloro-4-(4'-methoxyanilino)quinazoline (Compound No. 9)

5 ml of ethanol were added to a mixture of 4.8 g of 4,7-dichloroquinazoline and 3.0 g of p-anisidine. The resulting mixture was heated, whereupon the solids dissolved and then the mixture immediately solidified. After cooling, the solidified compound was collected and washed with, in turn, ethanol, dilute aqueous sodium hydroxide and water. The resulting crystals were recrystallized from ethanol to give 4.0 g (yield 51%) of the desired Compound No. 9 in the form of pale yellow plates melting at 177°–179° C.

Elemental Analysis: Calculated for $C_{15}H_{12}ON_3Cl.C_2H_5OH$: C, 61.54%; H, 5.47%; N, 12.66%. Found: C, 61.30%; H, 5.50%; N, 12.50%.

EXAMPLE 25

7-Chloro-4-(4'-methoxyanilino)quinazoline hydrochloride (Compound No. 10)

5 ml of ethanol were added to a mixture of 4.8 g of 4,7-dichloroquinazoline and 3.0 g of p-anisidine. The resulting mixture was heated, whereupon the solids dissolved and the reaction mixture immediately then solidified. After cooling, the solidified product was collected and washed with ethanol and the resulting crystals were recrystallized from ethanol, giving 2.0 g (yield 62%) of the desired Compound No. 10 in the form of a fine pale yellow powder having a melting point of 276°–279° C. (with decomposition).

Elemental Analysis: Calculated for $C_{15}H_{13}ON_3Cl_2$; C, 55.91%; H, 4.07%; N, 13.04%. Found: C, 55.50%; H, 4.00%; N, 12.80%.

EXAMPLE 26

4-(4'-Methoxyanilino)-7-trifluoromethylquinazoline (Compound No. 51)

5 ml of ethanol were added to a mixture of 2.3 g of 4-chloro-7-trifluoromethylquinazoline and 1.4 g of p-anisidine. The resulting mixture was heated to dissolve the solids, whereupon the solution solidified immediately. After cooling, the resulting crystals were collected by filtration and washed with, in turn, ethanol, dilute aqueous sodium hydroxide and water. The resulting crystals were recrystallized from ethanol, to give 2.5 g (yield 78%) of the desired Compound No. 51 in the form of colourless needles melting at 190°–194° C.

Elemental Analysis: Calculated for $C_{16}H_{12}ON_3F_3$: C, 60.18%; H, 3.76%; N, 13.16%. Found: C, 59.80%; H, 3.80%; N, 12.80%.

EXAMPLE 27

7-Chloro-4-(N-methylanilino)quinazoline hydrochloride (Compound No. 56)

A solution of 3.0 g of 4,7-dichloroquinazoline and 1.7 g of N-methylaniline in 10 ml of ethanol was heated for 10 minutes. After completion of the reaction, the ethanol was distilled off and the resulting crystals were recrystallized from a small amount of ethanol to give 2.4 g (yield 46%) of the desired Compound No. 56 in the form of pale yellow granules melting at 230°–233° C. (with decomposition).

Elemental analysis: Calculated for $C_{15}H_{13}N_3Cl_2$: C, 59.01%; H, 4.26%; N, 13.77%. Found: C, 58.95%; H, 4.20%; N, 13.80%.

EXAMPLE 28

7-Chloro-4-(N-ethylanilino)quinazoline hydrochloride (Compound No. 58)

A mixture of 3.0 g of 4,7-dichloroquinazoline and 2.0 g of N-ethylaniline in 10 ml of ethanol was heated for 5 minutes. After completion of the reaction the reaction mixture was cooled, whereupon crystals separated. These were collected by filtration and recrystallized from a small amount of ethanol to give 2.0 g (yield 47%) of the desired Compound No. 58 in the form of pale yellow needles melting at 222°–226° C. (with decomposition).

Elemental Analysis: Calculated for $C_{16}H_{15}N_3Cl_2$: C, 60.18%; H, 4.70%; N, 13.16%. Found: C, 60.00%; H, 4.85%; N, 13.10%.

EXAMPLES 29 and 30

Following the procedures described in Examples 27 and 28, the hydrochlorides shown in Table 5 were obtained.

TABLE 5

| Ex. No. | Cpd. No. | Melting Point | Appearance | Yield |
|---|---|---|---|---|
| 29 | 54 | 243–245° C. (decomposition) | pale yellow needles | 80% |
| 30 | 72 | 179–182° C. (decomposition) | pale yellow needles | 53% |

EXAMPLE 31

4-(N-Methylanilino)-7-trifluoromethylquinazoline (Compound No. 73)

2.5 g of 4-chloro-7-trifluoromethylquinazoline and 1.2 g of N-methylaniline were added, in turn, to 5 ml of ethanol, and then the mixture was heated until it became a homogeneous solution. At the end of this time, the ethanol was distilled off and the residual crystals were recrystallized from a 9:1 by volume mixture of ethanol and water, to give 1.4 g (yield 46%) of the desired Compound No. 73 in the form of colourless granules melting at 135°–137° C.

Elemental Analysis: Calculated for $C_{16}H_{12}N_3F_3$: C, 63.36%; H, 3.96%; N, 13.86%. Found: C, 63.25%; H, 4.00%; N, 14.05%.

EXAMPLE 32

7-Chloro-4-(4'-chloro-N-methylanilino)quinazoline (Compound No. 67)

2.5 g of 4,7-dichloroquinazoline and 2.2 g of p-chloro-N-methylaniline were added to 10 ml of ethanol and then the mixture was heated. The mixture became a homogeneous solution which solidified soon after. After cooling, the solidified crystals were collected and recrystallized from ethanol to give the desired compound in the form of its hydrochloride (Compound No. 68). The crystals of hydrochloride were crushed and added to a dilute aqueous solution of sodium hydroxide, with stirring, to precipitate the free base. The precipitate was collected by filtration, washed with water and recrystallized from ethanol to give 2.4 g (yield 65%) of the desired Compound No. 67 in the form of colourless plates melting at 129°–131° C.

Elemental Analysis: Calculated for $C_{15}H_{11}N_3Cl_2$: C, 59.40%; H, 3.63%; N, 13.86%. Found: C, 59.10%; H, 4.00%; N, 13.86%.

EXAMPLES 33–40

Following the procedures of Examples 31 and 32 the compounds listed in Table 6 were obtained; the compounds are identified in the Table by the numbers heretofore assigned to them.

TABLE 6

| Ex. No. | Cpd. No. | Melting point | Appearance | Yield |
|---|---|---|---|---|
| 33 | 55 | 103–105° C. | colourless granules | 65% |
| 34 | 61 | 118–120° C. | colourless flakes | 42% |
| 35 | 63 | 130–132° C. | colourless plates | 33% |
| 36 | 65 | 124–126° C. | colourless needles | 37% |
| 37 | 69 | 82–85° C. | colourless granules | 10% |
| 38 | 75 | 122–124° C. | colourless granules | 36% |
| 39 | 77 | 135–137° C. | pale yellow plates | 51% |
| 40 | 79 | 110–112° C. | yellow needles | 88% |

We claim:

1. A method of alleviating at least one of pain and inflammation in a mammal comprising administering to said mammal an agent selected from the group consisting of a compound of the formula (I) and pharmacologically acceptable acid addition salts thereof in an analgesic or anti-inflammatory effective amount:

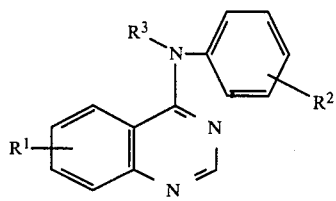

in which:

R¹ represents a hydrogen atom, a halogen atom, a trifluoromethyl group or a nitro group;

R² represents a hydrogen atom, a C₁–C₄ alkyl group, an alkoxy group or a halogen atom; and R³ represents a hydrogen atom or a C₁–C₄ alkyl group; provided that R¹ does not represent a hydrogen atom or a chlorine atom in a 6-position when R² and R³ both represent hydrogen atoms.

2. The method as claimed in claim 1, wherein said alkoxy group has from 1 to 4 carbon atoms.

3. The method as claimed in claim 1, wherein:
R¹ represents a hydrogen atom, or it represents a chlorine atom, a trifluoromethyl group or a nitro group at the 7- or 8-position;
R² represents a hydrogen atom or it represents a methyl group, an ethyl group, a methoxy group, an ethoxy group or a chlorine atom at the 4'-position; and
R³ represents a methyl group or an ethyl group.

4. The method of claim 1 wherein said agent is selected from the group consisting of 4-anilino-7-chloroquinazoline and pharmaceutically acceptable salts thereof.

5. The method of claim 4 wherein said agent is 4-anilino-7-chloroquinazoline.

6. The method of claim 1 wherein said agent is selected from the group consisting of 4-anilino-7-trifluoromethylquinazoline and pharmaceutically acceptable salts thereof.

7. 7-Chloro-4-(N-methylanilino)quinazoline and pharmaceutically acceptable salts thereof of the formula of claim 1.

8. The method of claim 1 wherein said agent is selected from the group consisting of 4-(N-methylanilino)-7-trifluoromethylquinazoline and pharmaceutically acceptable salts thereof.

9. A method of alleviating at least one of pain and inflammation in a mammal comprising administering to said mammal an agent selected from the group consisting of a compound of the formula (Ia) and pharmacologically acceptable acid addition salts thereof in an analgesic or anti-inflammatory effective amount:

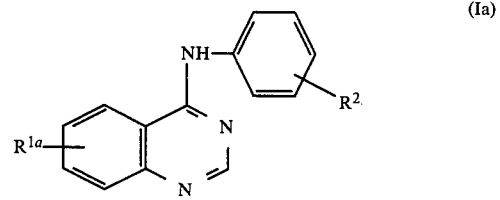

in which:

R¹ᵃ represents a halogen atom or a trifluoromethyl group; and

R² represents a hydrogen atom, a C₁–C₄ alkyl group, an alkoxy group having a C₁–C₄ alkyl moiety or a halogen atom; provided that R¹ᵃ does not represent a chlorine atom in the 6-position when R² represents a hydrogen atom.

10. The method as claimed in claim 9, wherein:
R¹ᵃ represents a halogen atom at the 7-position or a trifluoromethyl group at the 7- or 8-position; and
R² represents a hydrogen atom, a C₁–C₄ alkyl group, an alkoxy group having a C₁–C₄ alkyl moiety or a halogen atom.

11. The method as claimed in claim 9, wherein:
R¹ᵃ represents a chlorine atom at the 7-position or a trifluoromethyl group at the 7-or 8-position; and
R² represents a hydrogen atom, a methyl group, a methoxy group or a chlorine atom.

* * * * *

UNITED STATES PATENT AND TRADEMARK OFFICE
CERTIFICATE OF CORRECTION

PATENT NO. : 4,322,420
DATED : March 30, 1982
INVENTOR(S) : SHINSAKU KOBAYASHI et al It is certified that error appears in the above—identified patent and that said Letters Patent is hereby corrected as shown below:

Column 14, (Claim 7), line 1: before "7-Chloro-" insert
--The method of Claim 1 wherein said agent is selected from the group consisting of--.
line 2, delete "of the formula".
line 3, delete "of claim 1".

Signed and Sealed this

Seventeenth Day of January 1984

[SEAL]

Attest:

GERALD J. MOSSINGHOFF

Attesting Officer

Commissioner of Patents and Trademarks